US00PP30166P3

(12) United States Plant Patent
Danziger

(10) Patent No.: US PP30,166 P3
(45) Date of Patent: Jan. 29, 2019

(54) ***CALIBRACHOA* PLANT NAMED 'DCALCOPILA'**

(50) Latin Name: ***Calibrachoa* hybrid**
Varietal Denomination: DCALCOPILA

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 19 days.

(21) Appl. No.: 15/731,013

(22) Filed: Apr. 7, 2017

(65) Prior Publication Data

US 2018/0295765 P1 Oct. 11, 2018

(51) Int. Cl.
*A01H 5/02* (2018.01)
*A01H 6/82* (2018.01)

(52) U.S. Cl.
USPC ..... Plt./413
CPC ..... *A01H 6/821* (2018.05)

(58) Field of Classification Search
USPC ..... Plt./263.1, 413
See application file for complete search history.

(56) References Cited

PUBLICATIONS

Malmborg's Greenhouse Spring 2017. https://issuu.com/erin2350/docs/2017_catalog_online. Accessed Jun. 8, 2018. 4 pages.*

* cited by examiner

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Calibrachoa* cultivar named 'DCALCOPILA' is disclosed, characterized by a compact, mounded plant habit. Plants produce an abundance of large pink colored flowers with a yellow center and throat, darker veins, and small white stripes. Plants begin flowering early, have strong branches and are day length neutral. The new variety is a *Calibrachoa*, normally produced as an outdoor garden or container plant.

2 Drawing Sheets

Figure 1:
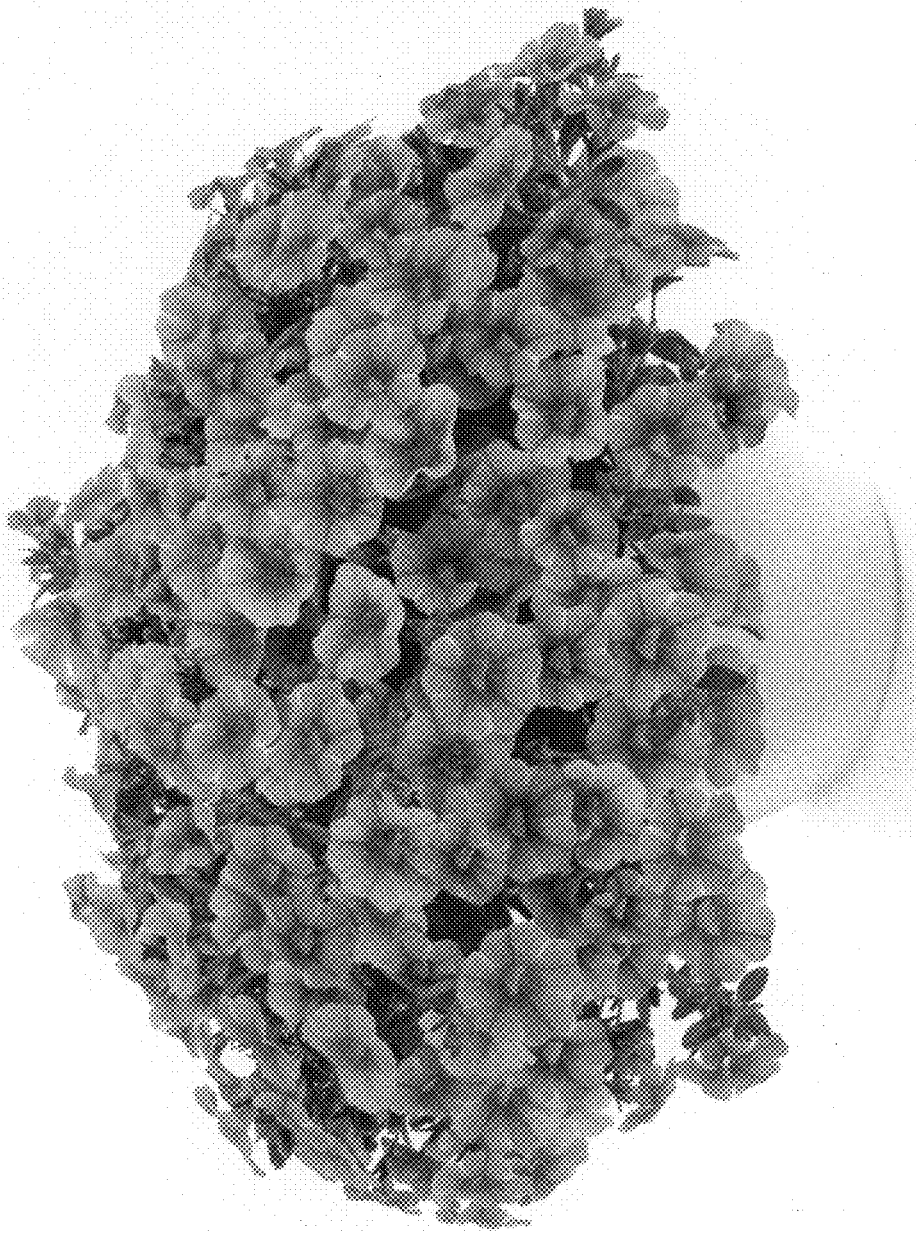

Latin name of the genus and species: *Calibrachoa* hybrid. Variety denomination: 'DCALCOPILA'.

BACKGROUND OF THE INVENTION

The new *Calibrachoa* cultivar is a product of a planned breeding program conducted by the inventor, Gavriel Danziger in Moshav Mishmar Hashiva, Israel. The objective of the breeding program was to produce new *Calibrachoa* varieties. The cross resulting in this new variety was made during November of 2013.

The seed parent is the unpatented, propriety variety referred to as *Calibrachoa* 'cv. 12-3332'. The pollen parent is the unpatented, propriety variety referred to as *Calibrachoa* 'cv. 12-3202'. The new variety was discovered in April of 2014 by the inventor in a group of seedlings resulting from the parental crossing, in a greenhouse in Moshav Mishmar Hashiva, Israel.

Asexual reproduction of the new cultivar 'DCALCOPILA' was first performed by terminal vegetative cuttings during May of 2016, at a greenhouse in Moshav Mishmar Hashiva, Israel. Subsequent propagation by has shown that the unique features of this cultivar are stable and reproduced true to type in successive generations.

SUMMARY OF THE INVENTION

The cultivar 'DCALCOPILA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DCALCOPILA' These characteristics in combination distinguish 'DCALCOPILA' as a new and distinct *Calibrachoa* cultivar:

1. Mounded and compact growth habit.
2. Early flowering.
3. Pink colored flowers with small white stripes and yellow throat.
4. Abundance of flowers.
5. Day length neutral flowering.
6. Strong branching.

PARENT COMPARISON

Plants of the new cultivar 'DCALCOPILA' are similar to plants of the seed parent in most horticultural characteristics, however, plants of the new cultivar 'DCALCOPILA' differ in the following;

1. The seed parent has a semi-trailing growth habit, the new variety is mounded.
2. Flower color of the seed variety is solid light pink, the new variety is medium pink with small white stripes and a yellow throat.
3. The new variety begins flowering much earlier than the seed parent Plants of the new cultivar 'DCALCOPILA' are similar to plants of the pollen parent in most horticultural characteristics however, plants of the new cultivar 'DCALCOPILA' differ in the following;

1. The pollen parent has a trailing growth habit whereas the new variety is mounded
2. The new variety has more branches than the pollen parent.
3. Pollen parent flower color is pink, the new variety flower color is pink with small white stripes and a yellow throat.
4. The pollen parent produces a moderate quantity of flowers, the new variety has an abundance of flowers.

COMMERCIAL COMPARISON

Plants of the new cultivar 'DCALCOPILA' can be compared to the patented commercial variety *Calibrachoa* 'Uscali51' U.S. Plant Pat. No. 14,874. These varieties are similar in most horticultural characteristics; however, 'DCALCOPILA' differs in the following:

1. The new variety begins blooming earlier than this comparator.
2. The new variety is day length neutral, this comparator is day length sensitive.
3. Flower color of the new variety is pink with small white stripes and yellow throat, this comparator is blue.
4. Plant habit of the new variety is mounded, 'Uscali51' is semi-trailing.

Plants of the new cultivar 'DCALCOPILA' can also be compared to the unpatented commercial variety *Calibrachoa* 'Calipetite White Improved', patent status unknown. These varieties are similar in most horticultural characteristics; however, 'DCALCOPILA' differs in the following:

1. Plants of the new variety are most vigorous than plants of this comparator.
2. Flower color of this comparator is white, the new variety is medium pink with small white stripes and a yellow throat.
3. The new variety has a larger flower than this comparator.

BRIEF DESCRIPTION OF THE PHOTOGRAPHS

The accompanying photograph in FIG. 1 illustrates in full color a typical plant of 'DCALCOPILA' grown in a greenhouse, in Moshav Mishmar Hashiva, Israel.

Figure 2:
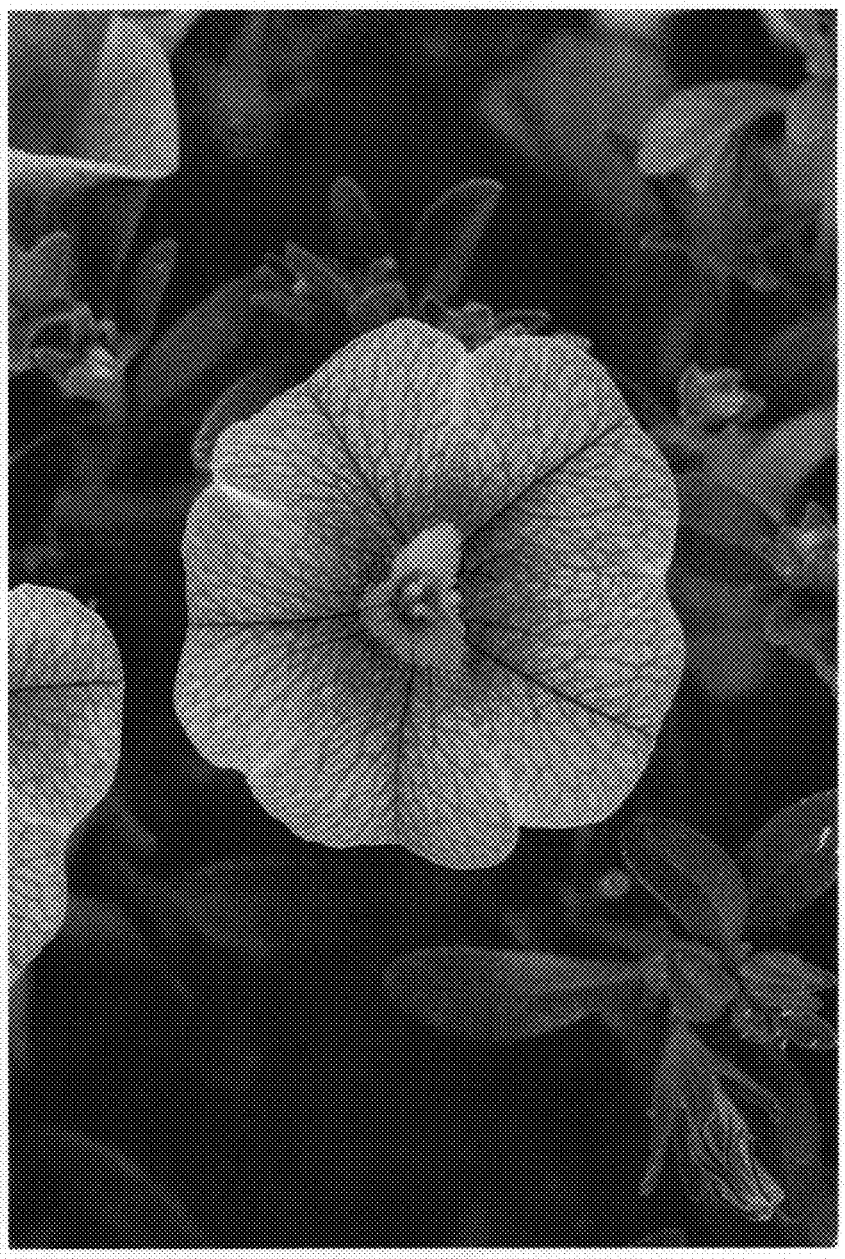

FIG. 2 illustrates in full color a close up of a typical flower of 'DCALCOPILA'. Age of the plant photographed is approximately 100 days from a rooted cutting in a 30 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DCALCOPILA' plants grown in greenhouse in Moshav Mishmar Hashiva, Israel, under natural lighting. Measurements were taken during Fall of 2016. The plants were approximately 60 days from a rooted cutting in a 13 cm pot. The growing temperature ranged from 15° C. to 28° C. during the days, 15° C. to 20° C. during the nights. Measurements and numerical values represent averages of typical plant types.

Botanical classification: *Calibrachoa* hybrid 'DCALCOPILA'.

PROPAGATION

Time to initiate roots: 10 to 15 days at approximately 18° C.

Root description: Densely fibrous. Brown, not accurately measured with an R.H.S. chart.

PLANT

Growth habit: Mounded.
Pot size of plant described: 13 cm.
Height: About 12 cm to top of flowering plane.
Plant spread: About 30 to 40 cm.
Growth rate: Moderate.
Branching characteristics: Very well branched.
Length of primary lateral branches: About 15 cm.
Diameter of lateral branches: About 0.3 cm.
Quantity of primary lateral branches: About 9 to 10.
Characteristics of primary lateral branches:
*Form*.—Cylindrical.
*Diameter*.—0.2 to 0.3 cm.
*Color*.—RHS Yellow-Green 146C.
*Texture*.—Scabrous.
*Strength*.—Strong, flexible.
Internode length: About 1.0 to 1.3 cm.

FOLIAGE

Leaf:
*Arrangement*.—Alternate.
*Quantity*.—Approximately 50 per branch.
*Average length*.—2.8 cm.
*Average width*.—1.0 cm.
*Shape of blade*.—Elliptic.
*Apex*.—Rounded.
*Base*.—Attenuate.
*Margin*.—Entire.
*Texture of top surface*.—Glabrous.
*Texture of bottom surface*.—Glabrous.
*Color*.—Young foliage upper side: RHS Yellow-Green 147B. Young foliage under side: RHS Yellow-Green 147B. Mature foliage upper side: RHS Yellow-Green 147A. Mature foliage under side: RHS Yellow-Green 147B.
*Venation*.—Type: Pinnate. Venation color upper side: RHS Yellow-Green 147A. Venation color under side: RHS Yellow-Green 147B.
*Petiole*.—Length: 1 to 2 mm. Diameter: 1.5 mm. Color: RHS Yellow-Green 147B. Texture: Glabrous.

FLOWER

Natural flowering season: Spring, Summer and Autumn in Beit Dagan, Israel.
Days to flowering from rooted cutting: About 20 to 30 days.
Inflorescence and flower type and habit: Axillary, single flower, salverform shape, upward and outwardly facing.
Rate of flower opening: 2 to 3 days from bud to fully opened flower.
Flower longevity on plant: 4 to 7 days.
Approximate quantity of flowers per plant: About 60.
Persistent or self-cleaning: Self-cleaning.

Bud:
*Shape*.—Ovoid.
*Length*.—About 2 cm.
*Diameter*.—About 0.3 cm.
*Color*.—RHS Yellow-green 147D.

Flower size:
*Diameter*.—About 3.5 to 4.0 cm.
*Length*.—About 3.5 cm.
*Flower tube diameter at distal end*.—About 0.5 cm.
*Flower tube diameter at proximal end*.—About 1.0 cm.

Petals:
*Length from throat*.—About 1.6 to 1.8 cm.
*Width*.—About 1.7 to 1.9 cm.
*Quantity*.—5.
*Texture*.—Glabrous.
*Apex*.—Notched.
*Margin*.—Entire.

Color:
*When opening*.—Upper surface: Main surface Red-Purple 70B. Veins 71A, stripe White N155C. Lower surface: Main surface Red-Purple N74D. Veins 71C.
*Fully opened*.—Upper surface: Main surface Red-Purple N74B. Veins 71A, stripe White N155C. Lower surface: Main surface Purple N78B. Veins N78A, stripe White N155C. Flower throat (inside): RHS Yellow 10A. Flower throat, vein: RHS Red-Purple 71A. Flower tube (outside): RHS Yellow 8C. Flower tube, vein: RHS Red-Purple 71A. Petal color, fading to: Main surface Red-Purple N74D. Veins 71A, stripe White N155C.

Calyx/Sepals:
*Quantity per flower*.—5.
*Shape*.—Lanceolate.
*Length*.—About 0.9 cm.
*Width*.—About 0.2 to 0.3 cm.
*Apex*.—Rounded.
*Base*.—Fused.
*Margin*.—Entire.
*Texture*.—Glabrous.
*Color*.—Upper Surface: RHS Yellow-Green 147A. Lower Surface: RHS Yellow-Green 147A.

Peduncle:
*Length*.—About 1.5 to 2.0 cm.
*Diameter*.—About 0.1 cm.
*Color*.—RHS Yellow-Green 147B.
*Texture*.—Pubescent.
*Orientation*.—45 degrees.

Fragrance: None.

REPRODUCTIVE ORGANS

Stamens:
*Number*.—5.
*Filament length*.—Average 7 mm.

Anthers:
*Length*.—About 0.1 cm.
*Shape*.—Globose.
*Color*.—RHS Yellow 9C.
*Pollen*.—Color: RHS Yellow 9D. Quantity: Scant.

Pistil:
*Number*.—1.
*Length*.—About 0.7 cm.
*Style*.—Length: About 0.6 cm. Color: RHS Yellow-Green 148C.
*Stigma*.—Shape: Oblate. Color: RHS Yellow-Green 148A. Ovary Color: RHS Yellow-Green 150B.

OTHER CHARACTERISTICS

Seeds and fruits: About 30 dark brown, rounded seeds of about 0.5 mm diameter, per one brown, conical capsule. Seed color close to 200A, capsule color close to 200D.

Disease/pest resistance: Typical to known *Calibrachoa* varieties. Neither resistance nor susceptibility to the normal diseases and pests of *Calibrachoa* have been observed. Pests common to *Calibrachoa* include Aphids and thrips. Typical diseases are *Botrytis* and *Pythium*.

Temperature tolerance: 5° C. to 30° C.

Drought tolerance: No tolerance for drought.

What is claimed is:

1. A new and distinct cultivar of *Calibrachoa* plant named 'DCALCOPILA' as herein illustrated and described.

* * * * *